(12) United States Patent
Rhew

(10) Patent No.: US 8,491,304 B2
(45) Date of Patent: Jul. 23, 2013

(54) DENTAL IMPLANT FIXTURE

(76) Inventor: Ill-Mo Rhew, Pyeongtaek (KR)

(*) Notice: Subject to any disclaimer, the term of this patent is extended or adjusted under 35 U.S.C. 154(b) by 129 days.

(21) Appl. No.: 11/995,284

(22) PCT Filed: Jul. 11, 2006

(86) PCT No.: PCT/KR2006/002727
§ 371 (c)(1),
(2), (4) Date: Jan. 10, 2008

(87) PCT Pub. No.: WO2007/008031
PCT Pub. Date: Jan. 18, 2007

(65) Prior Publication Data
US 2008/0213728 A1    Sep. 4, 2008

(30) Foreign Application Priority Data
Jul. 11, 2005 (KR) .................. 10-2005-0062391

(51) Int. Cl.
*A61C 8/00* (2006.01)
(52) U.S. Cl.
USPC ......... 433/174; 433/173; 433/172; 433/201.1
(58) Field of Classification Search
USPC ....... 433/172–176, 215–225, 201.1; 606/264, 606/275, 301–330; 411/378–426
See application file for complete search history.

(56) References Cited

U.S. PATENT DOCUMENTS

| 4,103,422 A * | 8/1978 | Weiss et al. ................. 433/215 |
| 6,406,295 B1 * | 6/2002 | Mahler ........................ 433/173 |
| 2002/0039717 A1 * | 4/2002 | Amber et al. ................. 433/172 |
| 2004/0063071 A1 * | 4/2004 | Schroering ................... 433/174 |
| 2004/0142304 A1 * | 7/2004 | Cottrell ........................ 433/173 |
| 2005/0014108 A1 * | 1/2005 | Wohrle et al. ................ 433/173 |
| 2005/0106534 A1 * | 5/2005 | Gahlert ........................ 433/173 |

FOREIGN PATENT DOCUMENTS

| JP | 2-041151 | 2/1990 |
| JP | 7328036 | 12/1995 |
| JP | 10211218 | 8/1998 |

OTHER PUBLICATIONS

International Search Report for corresponding International Application No. PCT/KR2006/002727 mailed Oct. 9, 2006.
Written Opinion of the International Searching Authority for corresponding International Application No. PCT/KR2006/002727 mailed Oct. 9, 2006.
Han, Jong-Hyun et al, "How can bone resorption be minimized in a dental implant?" Clinical Dentistry, 24(11), pp. 1360-1363 (2004).

(Continued)

*Primary Examiner* — Yogesh Patel
(74) *Attorney, Agent, or Firm* — Cantor Colburn LLP

(57) ABSTRACT

The present invention provides a fixture for a dental implant that serves as a replacement for a missing tooth and is implanted in the maxillary or mandibular bone. In this fixture invention the R/S border (the border between the rough and smooth surfaces) is formed to be inclined to a plane perpendicular to the long axis (central axis) of the dental implant fixture. The dental implant fixture prevents a marked decrease in the support for the dental implant due to bone reduction procedure in a patient having inclined bone crest, eliminates disadvantages in the aspects of expenses caused by the application of guided bone regeneration technique and also removes inconvenience of long operation time and possible infection, and also has a remarkable advantage of making convenient one-staged surgery possible in many cases.

6 Claims, 7 Drawing Sheets

OTHER PUBLICATIONS

Branemark, Per-Ingvar, Ed., Branemark Implant: Surgery, translated by Cho, Sung-Am, Chunji Publisher Company, Seoul, pp. A-14-15 (1997).

Kim, Young-Kyun and Hwang, Jung-Won, Various Controversies on Dental Implants, Koonja Publishers Company, Seoul, pp. 31-39 (2004).

Lee, Dong-Han, "What to choose for the surface morphology of implant fixture"? Journal of Korean Dental Association, 42(5), 2004.

Boucher, Carl O., Boucher's Prosthodontic treatment for endentulous patients. The C.V. Mosby Company (1985).

* cited by examiner

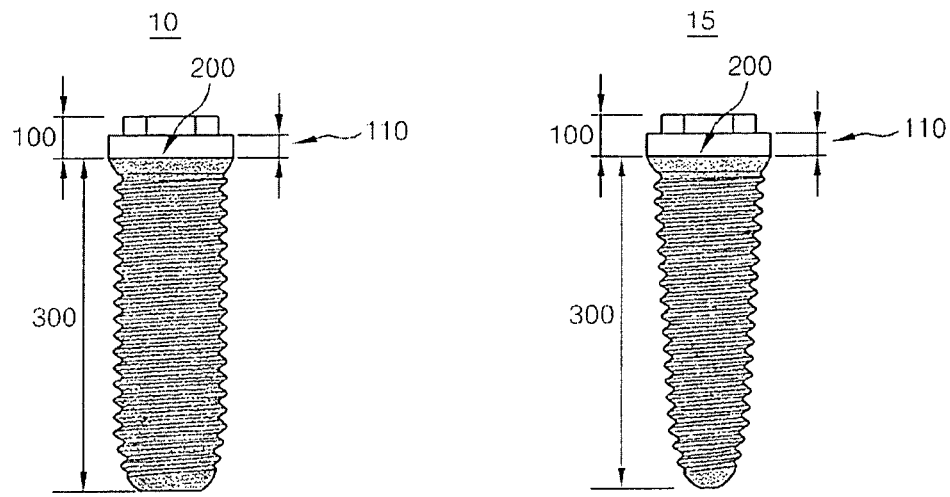
Fig. 1
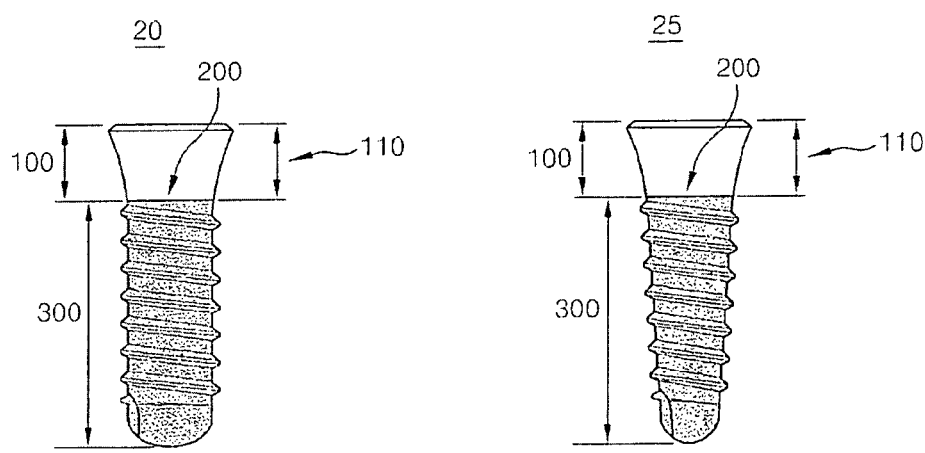
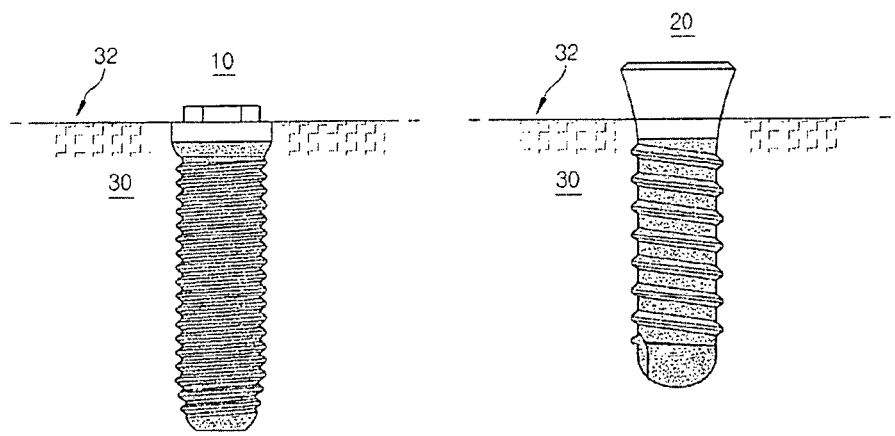
Fig. 2

Fig. 5
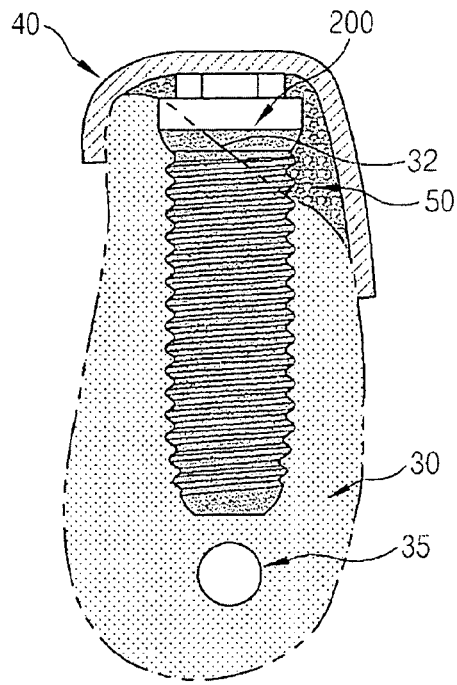
Fig. 6
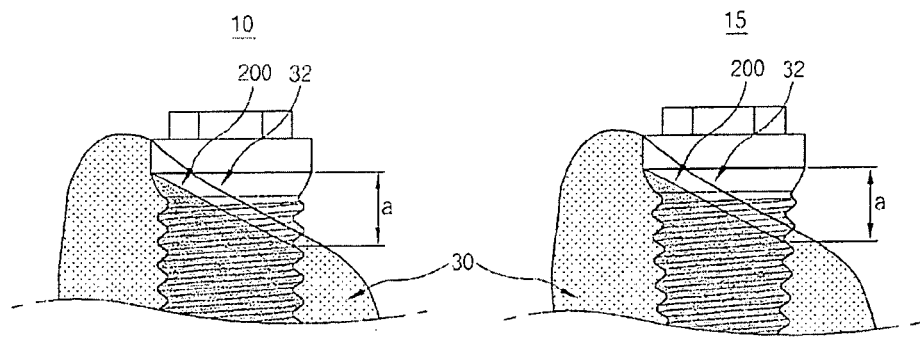
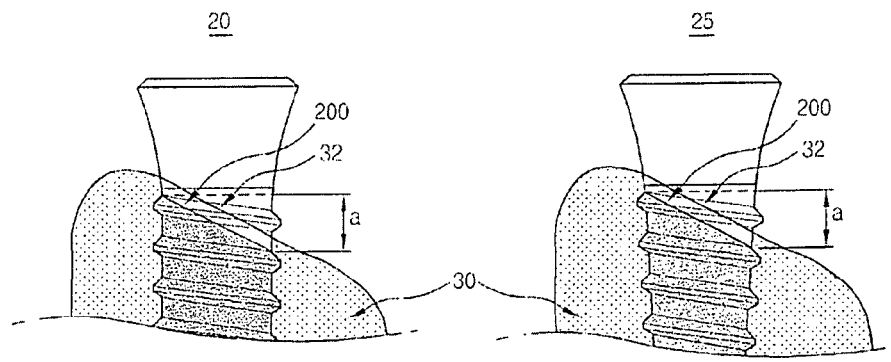

Fig. 11
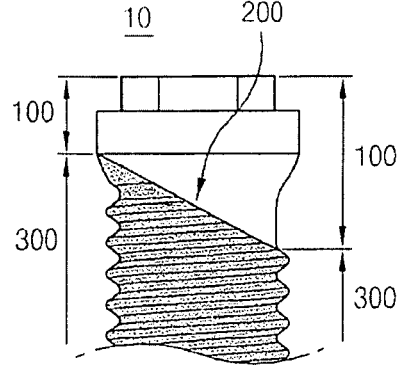
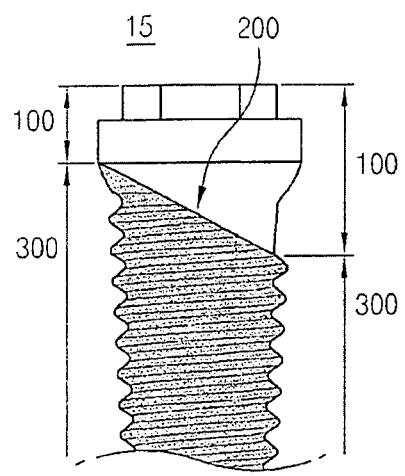
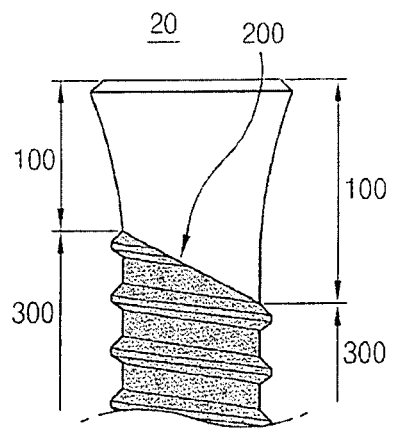
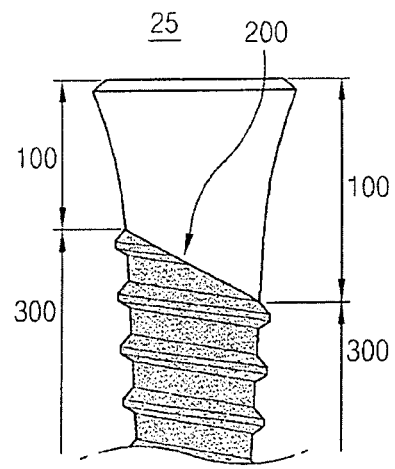

DENTAL IMPLANT FIXTURE

TECHNICAL FIELD

The present invention relates to the fixture of a dental implant that serves as a replacement for a missing tooth by being implanted in human maxillary or mandibular bone. In particular, this invention provides a dental implant fixture in which the border between the rough and smooth surfaces is fabricated to be inclined, for the treatment of patients having inclined bone crest on maxilla or mandible.

BACKGROUND ART

A dental implant is an artificial structure designed to replace a missing tooth. An artificial tooth root part of a dental implant, which is composed of biologically inert material, is made to be embedded and to adhere to the alveolar bone of the missing tooth. An artificial tooth crown part of a dental implant is then connected onto the artificial dental root so as to restore the original function of the missing tooth. A dental implant fixture is the artificial dental root part of a dental implant, which is made to be placed into the alveolar bone.

The dental implant fixtures of the early days had smooth surfaces formed by machining the surface of titanium rods. However, during the last decade researchers have focused on the development of a dental implant fixture having a certain roughness on the surface in order to enlarge the surface area contacting the maxillary or mandibular bone, and thus to achieve a high success rate even under the conditions of insufficient bone quality or quantity, to make it function properly within a short period of time and to be successful with a shorter length. Recently, it has been found that finishing the surface of a dental implant fixture with certain roughness has merits in biological aspects, not only by enlarging the area of mechanical contact with the bone, but also by accelerating the ossecintegration between bone and the dental implant fixture. Thus, the current market is substantially predominated by dental implant fixtures having rough surfaces (Lee, Dong-Han, "What to choose for the surface morphology of implant fixture?", *Journal of Korean Dental Association*, 42(5), 2004, published in the website: www.kda.or.kr; and Kim, Young-Kyun and Hwang, Jung-Won, *Various Controversies on Dental Implants*, Koonja Publishers Company, Seoul, pp. 31-39 (2004)). The issue about whether smooth surface is better or rough surface is better, is no longer a subject of dispute, and the current controversy is concerned in detailed issues such as the method of treatment to obtain rough surface, extent of roughness, appropriate location of the border between the rough and smooth surfaces (hereinafter, referred as R/S border), and the like.

A dental implant fixture having rough surface is more feasible to induce osseointegration and has a larger surface of contact with bone, while a dental implant fixture having smooth surface gives superior results in the reaction with soft tissue covering the bone (Kim and Hwang, ibid.). In particular, when a dental implant fixture having rough surface is exposed to the outside of the soft tissue barrier, which defends against bacterial invasion, the roughness of the surface causes accumulation of plaque (bacterial membrane on the tooth surface) more easily than the smooth surface, thus inducing periodontitis and subsequent loss of alveolar bone, and also increasing the risk of implant failure in the long term (Kim and Hwang, ibid.). Accordingly, most of the dental implant fixtures having rough surfaces are designed to have smooth-surfaced collars/cuffs in the coronal part, where the dental implant fixture is brought into contact with the soft tissue (FIG. 1). In case a dental implant fixture has no smooth surface in the coronal part, the dental implant fixture is usually designed to have a smooth surface contacting with the soft tissue, at the apical end of the dental implant abutment where the abutment joins with the fixture.

Such dental implant fixtures have their placement protocols which say the R/S borders, all designed to be horizontal although their vertical locations vary depending on companies, should be placed at a position lower than the bone crest (the highest part of the alveolar bone). The objects of these placement protocols are to protect the rough surfaces of the dental implant fixtures from bacterial attack by placing the rough surfaces inside of the bone. This serves as a secondary protective barrier to bacterial attack. So, even when the gingiva which serves as a primary protective barrier to bacterial attack has been destroyed by periodontitis, etc., the rough surfaces can be safe inside of the bone. Such placement protocols have been established because exposure of the rough surface of the dental implant fixture to the bacteria in oral cavity could be fatal to the survival of implant (FIG. 2).

When the gingiva is incised and the crestal bone is exposed for the purpose of implant placement, the crestal bone is often inclined downward from the lingual side toward the buccal side, more often than the cases where the crestal bone is flat and horizontal. This is because bone resorption due to disuse atrophy of the maxillary or mandibular bone occurs more actively on the buccal side after loss of a tooth. Such inclination occurs more frequently in the mandibular bone compared to the maxillary bone (Branemark, Per-Ingvar, Ed., *Branemark Implant: Surgery*, translated by Cho, Sung-Am, Chunji Publisher Company, Seoul, pp. A-14-15 (1997); and Hickey, Judson C., et al., *Boucher's Prosthodontic Treatment for Edentulous Patients*, Warfel, Darlene, et al., Ed., The C.V. Mosby Company, Missouri, p. 181 (FIG. 9-9) (1985)).

When the crestal bone is inclined as described above, dental implant fixtures having horizontal R/S borders have some portion of their rough surfaces exposed to the outside of the bone crest, when placed without any special treatment (FIG. 3).

In order to prevent such exposure, part of the bone protruded upward (the portion above the dotted line in the left diagram of FIG. 4) should be removed to flatten the crestal bone as illustrated in FIG. 4, or alternatively, guided bone regeneration should be performed at the inclined part of the crestal bone as illustrated in FIG. 5.

Successful implant placement necessitates factors such as provision of sufficient mechanical and physical support. In this regard, placements of longer dental implant fixtures are advantageous. However, the above-described method of removing the protruded part of bone involves placement of a dental implant fixture shortened by a length equal to the length of the removed bone part, and this shortened Length of the dental implant fixture can adversely affect the success of implant placement. In particular, when the distance from the inferior alveolar nerve in the mandibular bone to the bone crest is so short that the length of the dental implant fixture is restricted thereby, removing the part of crestal bone as such is obviously highly unfavorable. The above-described method of performing guided bone regeneration requires significant additional expenses for the use of artificial bone graft and barrier membrane, requires prolonged operation time and patient inconvenience, and increases possibilities for infection and subsequent implant failure.

DISCLOSURE OF THE INVENTION

Technical Problem

An object of the present invention is to address such problems existing in conventional dental implant fixtures that serve as replacements of missing teeth in human maxillary or mandibular bones, and to provide fixture which has the R/S border (border between the rough and smooth surfaces) formed to be inclined for the treatment of patients having inclined bone crest.

Technical Solution

In order to achieve the object as described above, the present invention provides a dental implant fixture comprising a rough-surfaced lower part having a predetermined roughness, and a smooth-surfaced upper part having a roughness lower than the roughness of the rough-surfaced lower part, wherein a plane containing the R/S border (the border between the rough and smooth surfaces) is formed to be inclined to a plane perpendicular to the long axis (central axis) of the dental implant fixture.

According to an embodiment of the present invention, the difference between the maximum height and the minimum height of the rough surface in the direction parallel to the long axis of the dental implant fixture is in the range of 1 to 3 mm.

According to another embodiment of the present invention, an identification mark is formed on the upper surface of the dental implant fixture, and the identification mark indicates the direction toward the minimum height or maximum height of the rough surface of the dental implant fixture.

According to another embodiment of the present invention, fixture threads are formed only on the rough surface of the dental implant fixture.

According to another embodiment of the present invention, microgrooves are formed on the smooth surface of the dental implant fixture.

Advantageous Effects

The dental implant fixture of the present invention which has the inclined R/S border to the plane perpendicular to the long axis of the dental implant fixture, is remarkably effective in preventing any reduction in the implant stability caused by a bone removal procedure in patients having inclined bone crest, and in eliminating disadvantages in the aspects of expenses caused by guided bone regeneration, inconvenience of operation, and possible infection. The dental implant fixture of the present invention is also highly advantageous when a practitioner uses one-staged approach.

BRIEF DESCRIPTION OF THE DRAWINGS

FIG. 1 is a front view of a conventional dental implant fixture.

FIG. 2 is a diagram illustrating the status of a conventional dental implant fixture placed in the bone.

FIG. 5 is a diagram for illustrating a method for implant placement through guided bone regeneration.

FIG. 6 is a diagram illustrating the status of a dental implant fixture according to an embodiment of the present invention placed in a bone having inclined bone crest.

FIG. 11 is a top front view of a dental implant fixture according to an embodiment of the present invention, in which fixture threads are formed only on the rough surface.

BEST MODE FOR CARRYING OUT THE INVENTION

Hereinafter, embodiments of the present invention will be described in more detail with reference to attached drawings.

FIG. 6 is a diagram illustrating the status of a dental implant fixture according to an embodiment of the present invention placed in a bone having inclined bone crest. As illustrated in FIG. 6, the R/S border of the dental implant fixture of the present invention is formed at an angle to the horizontal. Such formation of the R/S border is intended, when placing a dental implant fixture in a not too excessively inclined bone crest, to place the rough surface of the dental implant fixture inside the bone without removing any protruded bone part or performing guided bone regeneration.

Figure 3:
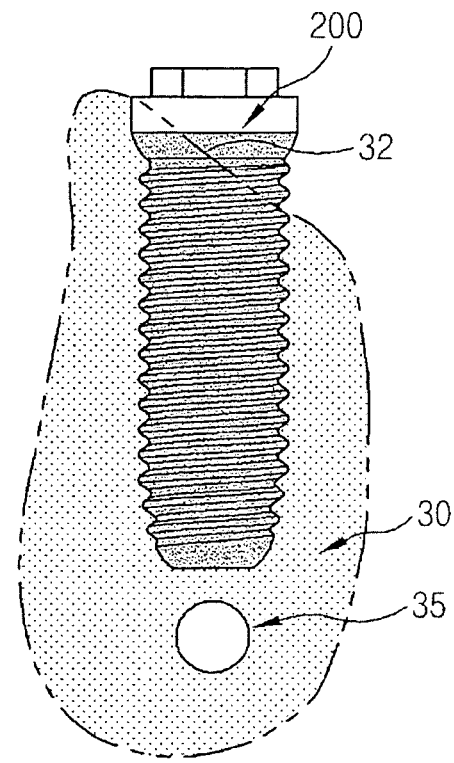
FIG. 3 is a diagram illustrating the status of a conventional dental implant fixture placed in a bone having inclined bone crest.
Figure 4:
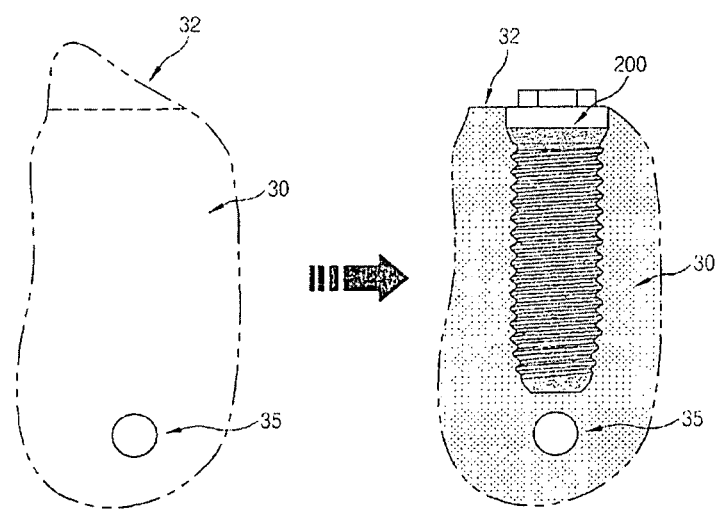
FIG. 4 is a diagram for illustrating a method for implant placement through bone reduction procedure.
Figure 7:
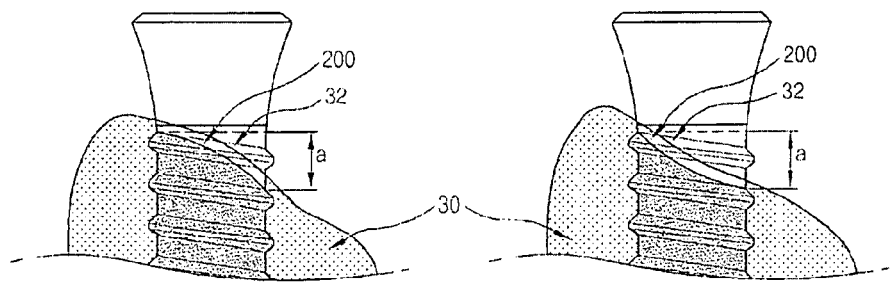
FIG. 7 is a partial front view of a dental implant fixture according to an embodiment of the present invention, in which the R/S border is curved.
Figure 8:
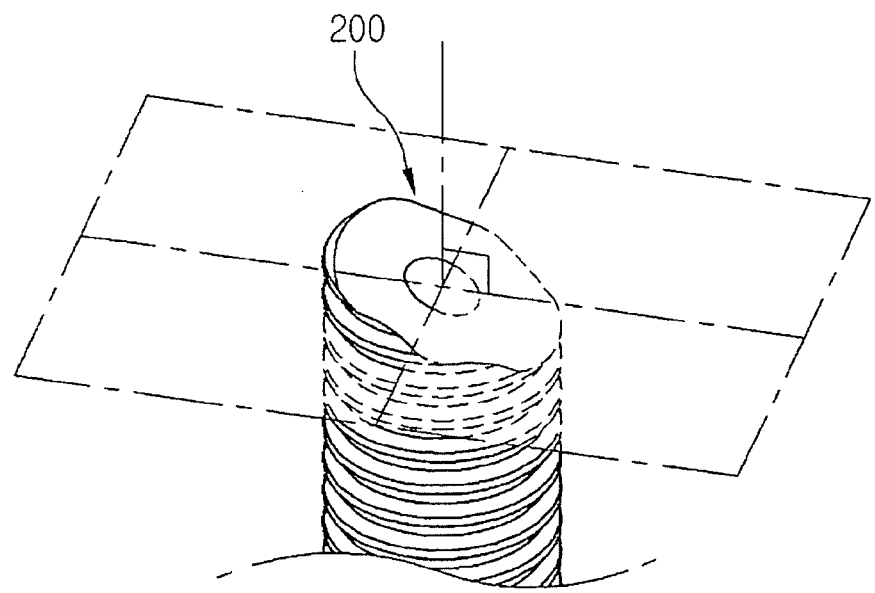
FIG. 8 is a conceptual diagram illustrating the status in which a plane containing the R/S border intercepts a plane perpendicular to the long axis of the dental implant fixture of the present invention.

To this end, the dental implant fixture 10 or 20 of the present invention comprises a rough-surfaced lower part 300 having a predetermined roughness and a smooth-surfaced upper part 100 having a roughness lower than the roughness of the rough-surfaced lower part, and a plane containing the R/S border 200 is formed inclined to the plane perpendicular to the long axis of the dental implant fixture. The plane containing the R/S border 200 can be planar as illustrated in FIG. 6, or can be curved as illustrated in FIG. 7. Here, the phrase "(the plane containing the R/S border 200) is formed to be inclined to a plane perpendicular to the long axis of the dental implant fixture" implies that the plane containing the R/S border 200 intercepts a plane perpendicular to the long axis of the dental implant fixture on a single line, as illustrated in FIG. 8.

The dental implant fixture having an inclined R/S border 200 in accordance with the inclined bone crest 32 is advantageous in the following aspects.

First, it is not necessary to remove the protruded part of the crestal bone, thus this protruded bone part can be utilized for supporting the dental implant fixture more firmly.

Secondly, a large amount of expenses needed for the guided bone regeneration procedure can be saved.

Thirdly, the time and effort needed to perform the guided bone regeneration technique can be much reduced, thus the convenience of operation for both the patient and the dentist can be increased significantly.

Fourthly, the possibilities of infection that is often associated with the guided bone regeneration technique and of the subsequent failure of the dental implant itself can be reduced.

Fifthly, it can make one staged approach (the placement and the exposure through gingiva of the fixture are done at the same time) possible in some cases by removing the necessity of using the guided bone regeneration technique. When the guided bone regeneration technique is to be used, the dental implant fixture should be completely embedded in the gingiva during the first-stage operation to prevent infection. And the embedded dental implant fixture needs to be exposed to the outside of the gingiva after several months through second surgery. Thus, the operation is to be performed two times.

Sixthly, when there is no peri-implant keratinized gingiva (gingiva associated with the presence of hard keratin is more resistant to mechanical stimulation or bacterial invasion), it is a general practice in dentistry to harvest keratinized gingiva from the palate and transplant the harvested keratinized gingiva to the site of implant placement in order to assure success of the dental implant in the long term. However, a number of research reports suggest that the presence or absence of keratinized gingiva does not seriously affect the success of implant placement in the long term, and there are widely accepted research results that in particular, dental implant fixtures having smooth surfaces show equal success rates without transplantation of keratinized gingiva. By placing the broad smooth surface of the inclined R/S border of the dental implant fixture of the present invention, at a site lacking keratinized gingiva, a result equivalent to the result of using a smooth surfaced dental implant can be obtained, and thus, the procedure of transplanting/grafting keratinized gingiva can be skipped.

A dentist performing implant placement would mainly use those conventional dental implant fixtures having horizontal R/S borders and could keep the dental implant fixtures of the present invention having inclined R/S borders as supplements. Then, the dentist may selectively, and also advantageously, use the dental implant fixtures of the present invention for the sites where slight inclined bone crest is, where guided bone regeneration is not necessary, and where slight recession of the gingiva is not considered as a serious esthetic defect or esthetic aspects are less important, such as mandibular posterior areas or maxillary posterior areas.

Meanwhile, the difference between the maximum height and the minimum height (represented by symbol a in FIG. 6 and FIG. 7) of the rough surface in the direction parallel to the long axis of the dental implant fixture, is preferably in the range of 1 to 3 mm. When this difference is less than 1 mm, the inclination is virtually negligible, so the application of inclined R/S border isn't necessary. When the difference exceeds 3 mm, a large surface of fixture is out of contact with the bone, so it is unfavorable in terms of bony support.

Figure 9:
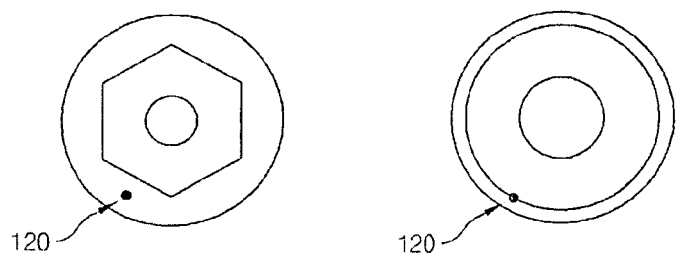
FIG. 9 is a planar view of a dental implant fixture according to an embodiment of the present invention having an identification mark.

FIG. 9 is a planar view of a dental implant fixture according to an embodiment of the present invention, having an identification mark formed thereon.

Meanwhile, the dental implant fixture 10 or 20 of the present invention is characterized in that an identification mark 120 is formed on the upper surface, and this identification mark 120 indicates the direction toward the minimum height or maximum height of the rough surface.

Since the reliability and predictability of dental implant fixtures have been already sufficiently established, the issue at hand is about how to provide convenience of operation to the dentist and less invasive treatment to the patient. Therefore, in recent years, an operation technique of perforating a small hole in the gingiva with a tissue punch or the like, without directly incising the gingiva, and placing a dental implant fixture through the punched hole, thus eliminating the need for suturing and reducing the post-operative pain in the patient significantly, is being widely employed. In this operation technique, the R/S border 200 of the dental implant fixture 10 or 20 may be shielded by the gingiva during the implant placement and remain out of sight, while the conventional operation techniques allow a full view of the R/S border by means of sufficient incision of the gingiva. In that case, the dentist performing the operation can look at the upper surface of the dental implant fixture 10 or 20, or the upper surface of a fixture mount 40, specifically the identification mark 120 formed on the shoulder part of the dental implant fixture 10 or 20 or on the fixture mount 40, and locate the inclined R/S border 200 at a desired site.

Figure 10:
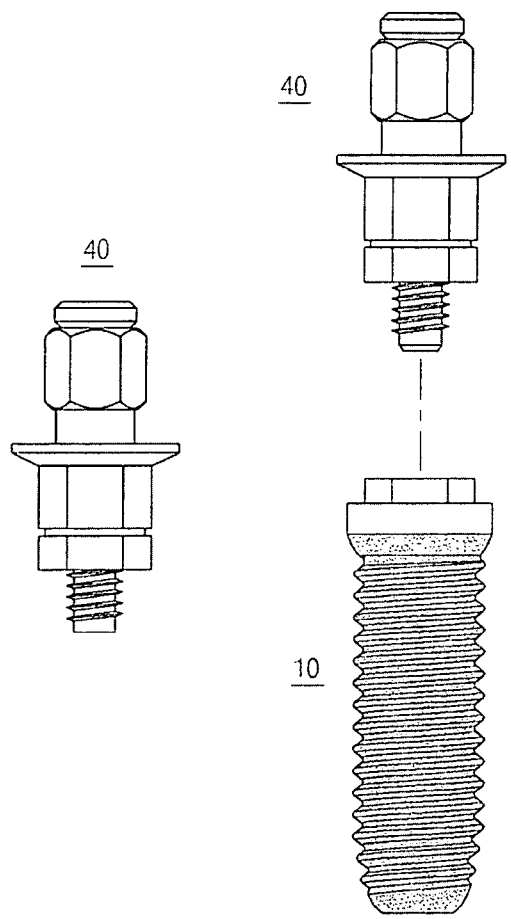
FIG. 10 is a front view of a fixture mount, and a diagram illustrating the status in which the fixture mount is joined with a dental implant fixture according to an embodiment of the present invention.

Here, the fixture mount 40 is an element designed to detachably join with the upper surface of the dental implant fixture 10 or 20, as illustrated in FIG. 10. This element prevents any deformation of the dental implant fixture 10 or 20 that can possibly occur when a force is directly exerted to the dental implant fixture 10 or 20 by an instrument used to rotate the dental implant fixture 10 or 20 during placement in the bone, and secures an area of exposure, apart from the dental implant fixture 10 or 20, to provide a site to which the instrument for rotating the dental implant fixture can transfer a rotating force, in the case where the placement has proceeded to a great extent.

Here, it is preferable to have an identification mark 120 on the upper surface of the dental implant fixture, when the instrument for rotating the dental implant fixture is directly attached to the dental implant fixture 10 or 20; while it is preferable to have an identification mark 120 on the upper surface of the implant fixture mount 40, when the instrument is attached to the fixture mount 40.

FIG. 11 is a front view of the upper part of a dental implant fixture according to an embodiment of the present invention, having a fixture thread formed only on the rough surface.

The thread of the dental implant fixture 10 or 20 can be formed only on the rough surface. That is, the smooth surface of the dental implant fixture 10 or 20 is maintained as a cylindrical surface without any thread or grooves. This is because a smooth surface having no thread is more advantageous in adhering to the soft tissue, and causes less plaque deposition, and therefore better resistance to periodontitis, compared with a surface having threads, even in the case where the attachment of the dental implant fixture to the soft tissue fails and the dental implant fixture is exposed to the outside.

Figure 12:
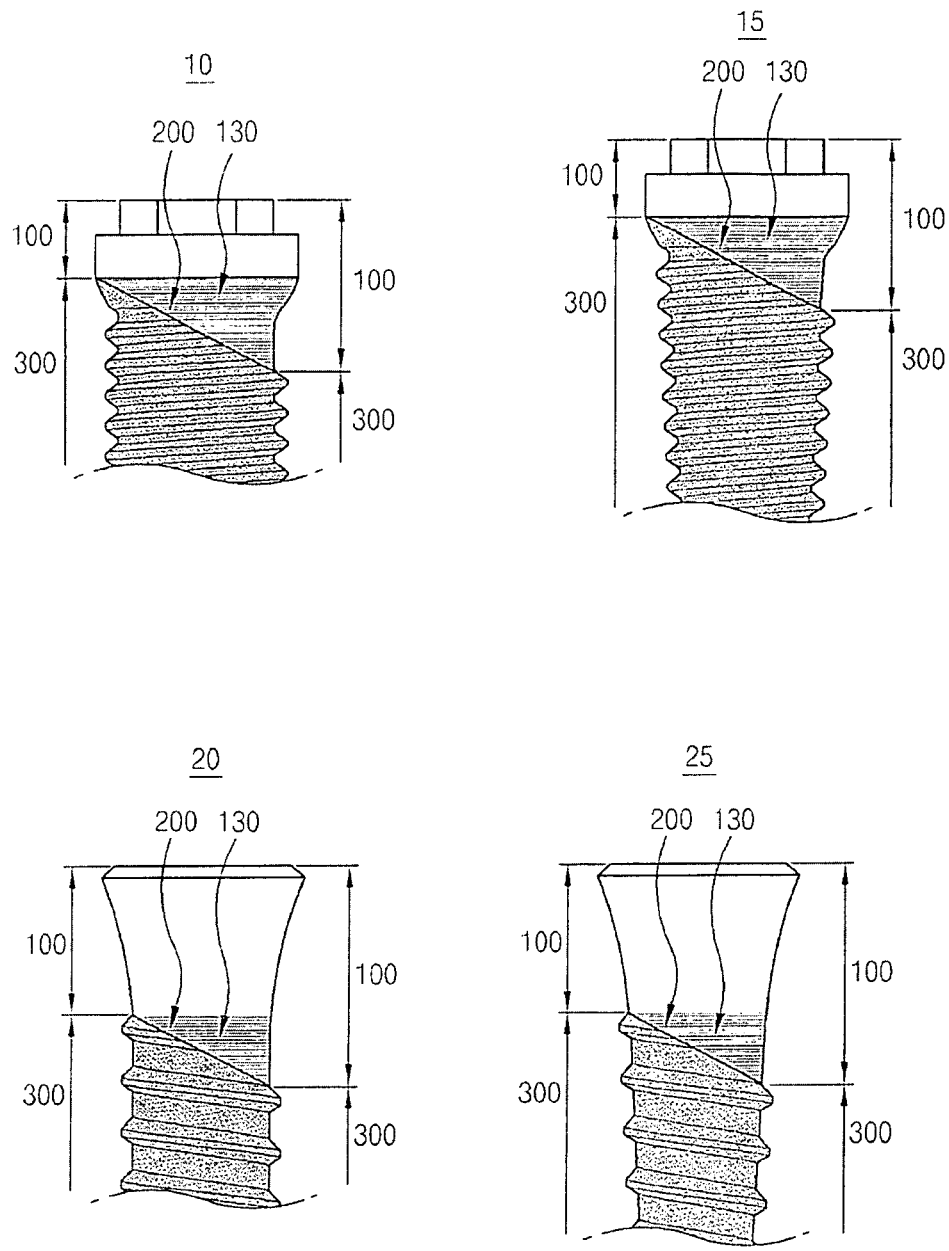
FIG. 12 is a top front view of a dental implant fixture according to an embodiment of the present invention, in which microgrooves are formed on the smooth surface.

FIG. 12 is a front view of the upper part of a dental implant fixture 10 or 20 according to an embodiment of the present invention, having microgrooves 130 formed on the smooth surface.

The dental implant fixture of the present invention can have microgrooves 130 formed on the smooth surface, instead of a screw thread.

Microgrooves 130 facilitate stronger attachment of the connective tissue in the gingiva to the smooth surface of the dental implant fixture (Han, Jong-Hyun, et al., "How can bone resorption be minimized in a dental implant?", *Clinical Dentistry*, 24(11), pp. 1360-1363 (2004)).

Heretofore, while the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:
1. A dental implant fixture comprising:
a rough-surfaced lower part having a predetermined roughness; and
a smooth-surfaced upper part having a roughness lower than the predetermined roughness of the rough-surfaced lower part, wherein an interface of the rough-surfaced lower part with the smooth-surfaced upper part defines a plane therebetween, the plane is inclined with respect to an imaginary plane aligned perpendicular to a longitudinal central axis of the rough-surfaced lower part of the dental implant fixture, and a screw thread is formed on a rough surface of the rough-surfaced lower part.

2. The dental implant fixture according to claim 1, wherein a rough surface of the rough-surfaced lower part has a maximum height and a minimum height in a parallel direction to the longitudinal central axis of the rough-surfaced lower part of the dental implant fixture, and the difference between the maximum and minimum heights is in the range of 1 mm to 3 mm.

3. The dental implant fixture according to claim 2, further comprising an implant fixture mount,
wherein an identification mark is formed on an upper surface of the dental implant fixture or on an upper surface of the implant fixture mount, and the identification mark indicates a direction toward the minimum height or the maximum height of the rough surface.

4. The dental implant fixture according to claim 2, wherein microgrooves are formed on a smooth surface of the smooth-surfaced upper part.

5. The dental implant fixture according claim 1, wherein an upper surface of the dental implant fixture is perpendicular to the longitudinal central axis of the rough-surfaced lower part of the dental implant fixture.

6. A dental implant fixture comprising:
a rough-surfaced lower part having a predetermined roughness; and
a smooth-surfaced upper part having a roughness lower than the predetermined roughness of the rough-surfaced lower part,
wherein an interface of the rough-surfaced lower part with the smooth-surfaced upper part defines a plane therebetween, the plane is inclined with respect to an imaginary plane aligned perpendicular to a longitudinal central axis of the rough-surfaced lower part of the dental implant fixture, a screw thread is formed on a rough surface of the rough-surfaced lower part and is formed on a part of a smooth surface of the smooth-surfaced upper part, and an upper surface of the dental implant fixture is perpendicular to the longitudinal central axis of the rough-surfaced lower part of the dental implant fixture.

* * * * *